United States Patent [19]
Daikuzono

[11] Patent Number: 5,470,331
[45] Date of Patent: Nov. 28, 1995

[54] LASER LIGHT IRRADIATION APPARATUS FOR MEDICAL TREATMENT

[75] Inventor: Norio Daikuzono, Chiba, Japan

[73] Assignee: S.L.T. Japan Co., Ltd., Tokyo, Japan

[21] Appl. No.: 176,372

[22] Filed: Dec. 30, 1993

Related U.S. Application Data

[62] Division of Ser. No. 761,892, Sep. 12, 1991, Pat. No. 5,328,488.

[30] Foreign Application Priority Data

Mar. 31, 1990 [JP] Japan ................................ 2-12347

[51] Int. Cl.$^6$ ............................................. A61B 17/32
[52] U.S. Cl. ........................... 606/16; 606/13; 606/17
[58] Field of Search ........................... 606/8, 9, 13, 14, 606/15, 16, 17, 52; 604/21, 22; 607/88, 89, 90, 91

[56] References Cited

U.S. PATENT DOCUMENTS

| | | |
|---|---|---|
| 2,186,143 | 3/1939 | Neugass . |
| 3,834,391 | 9/1974 | Block . |
| 4,240,431 | 12/1980 | Komiya . |
| 4,249,136 | 11/1978 | Auth et al. . |
| 4,249,533 | 2/1981 | Komiya . |
| 4,266,547 | 5/1981 | Komiya . |
| 4,273,127 | 6/1981 | Auth et al. . |
| 4,736,743 | 4/1988 | Daikuzono . |
| 5,129,897 | 7/1992 | Daikuzono . |
| 5,139,495 | 8/1992 | Daikuzono . |

FOREIGN PATENT DOCUMENTS

| | | |
|---|---|---|
| 0069351 | 1/1983 | European Pat. Off. . |
| 0070459 | 1/1983 | European Pat. Off. . |

*Primary Examiner*—Stephen C. Pellegrino
*Assistant Examiner*—Sonya Harris-Agugua
*Attorney, Agent, or Firm*—Lowe, Price, LeBlanc & Becker

[57] ABSTRACT

Laser light apparatus for medical treatment to permit amputations, incisions, vaporization of living tissues of an animal such as a human body, thermal therapy and the like. This apparatus consists of a laser light generator, a laser light transmissive probe system and a laser light transmitting system. The laser light transmissive probe system is provided with an opposed pair of laser light transmissive probes. The opposed pair of probes can be controlled by a medical operator so as to be moved into or out of contact with each other at their laser light emitting portions. Laser light is transmitted to the opposed pair of probes from the laser light generator through the laser light transmitting system. Then, a target area of living tissues is pinched by the opposed pair of laser light transmissive probes so as to be disposed between the opposed pair of laser light emitting portions.

14 Claims, 17 Drawing Sheets

BV

BV

BV                BV

LASER LIGHT IRRADIATION APPARATUS FOR MEDICAL TREATMENT

This application is a division of application Ser. No. 07/761,892 filed Sep. 12, 1991 now U.S. Pat. No. 5,328,488.

TECHNICAL FIELD

This invention relates to laser light apparatus for medical treatments to permit amputations, incisions, vaporization of living tissues of an animal such as a human body, thermal therapy and the like, particularly to laser light apparatus for medical treatments with good characteristics for amputations, hemostasis and anastomosis.

PRIOR ART

Medical treatments such as incisions of living tissues of animal organisms by irradiation with laser light have become common due to the hemostasis which laser treatments provide.

The conventional method has been that the laser light is irradiated from the fore end of an optical fiber which is held back out of contact with the living tissues. But this method causes severe damage to the fore end portion of the optical fiber. Therefore, a method which has been utilized lately is as discussed below.

First, laser light is transmitted into an optical fiber, whose fore end portion is located adjacent to treated living tissues. Next, the laser light fed out from the optical fiber is fed into an emitting probe, which is held in or out of contact with the living tissues. Then, the laser light is emitted from the surface of the probe for irradiating against the living tissues. In this case, the probe should be brought into contact with the living tissues (hereafter "living tissue" is sometimes expressed by "tissue" only).

The inventor developed many kinds of such contact probes which are utilized for various purposes.

When the tissues are incised with these contact probes, the tissues should be incised along an incision line repeatedly on the upper side surface of the tissues. When a blood vessel having smaller diameter is amputated, bleeding is not caused so much, because, a target area of the blood vessel is coagulated by the laser light irradiation. However, when a blood vessel having a diameter larger than 1.5 mm is amputated, often the blood vessel should be previously tied at the both sides of the target area with a medical thread.

That is to say, if that single transmitting probe is used for amputating the thick blood vessel, the above mentioned tying of the blood vessel is required every time. Accordingly, it takes a long time to perform a medical operation. Further, a more severe problem is as follows; even if the medical thread used in the tying is fused into the living body after recovery of a patient, the thread often can not be fused completely. In this case, the patient should be operated on again for removing the medical thread, which is large burden to the patient's body.

In an incision of hemorrhagic tissues such as the liver and the like with laser light irradiation, the probe must be repeatedly moved along an incision line little by little in order to suppress the bleeding caused at the target area as much as possible. Therefore, the medical operation requires much labor and must be done carefully.

Generally, in order to eliminate bleeding problems in incising or amputating tissues, laser light should be irradiated many times. However, at the end of an incision line where incised tissues and un-incised normal tissues are adjacent each other, the laser light is often irradiated against the normal tissues by mistake. Accordingly, the normal tissues are damaged.

On the other hand, for removing a projected tumor, a ring-shaped high frequency snare is provided so as to encircle the tumor. Then, the tumor is amputated at its root with the snare. However, this treatment can not be carried out with a high level of hemostasis. Also, if physiological saline solution is used in this treatment, electrical shock may be given to a patient. Furthermore, tissues around the tumor are often burned. As a result, the tissues are damaged.

It is therefore the main object of the present invention to provide laser light irradiation apparatus for medical treatments, which can amputate and incise a target area of tissues with single operation with a high level of hemostasis, while laser light is not irradiated against other normal tissues, and which can amputate a blood vessel without tying. In other words, it is the main object of the present invention to provide the laser light irradiation apparatus, by which medical operation can be finished in short time.

DISCLOSURE OF THE INVENTION

In the present invention, a laser light irradiation apparatus consists of a laser light generator, a laser light penetrating probe system and a laser light transmitting system. The laser light transmissive probe system is provided with an opposed pair of laser light transmissive probes. The opposed pair of probes can be controlled by a medical operator so that their opposed pair of laser light emitting portions are held in or out of contact with each other. Laser light impinges onto the pair of light transmissive probes from the laser light generator through the laser light transmitting system. Then, a target area of tissues is pinched by the pair of penetrating probes so as to be disposed between the opposed pair of laser light emitting portions.

The laser light can be irradiated against the target-area of a blood vessel and the like from both sides thereof while the target area is pinched by the opposed pair of laser light penetrating probes which can be used like a pincette. Accordingly, abilities of this apparatus of the present invention in amputating and incising are improved so as to be at least two times of the abilities of conventional apparatus. Additionally another surprising advantage can be obtained by this apparatus. A blood vessel having a diameter larger than a certain length can not be amputated with single probe without bleeding. However, the blood vessel can be amputated easily with the opposed pair of laser light penetrating probes of the present invention. Further, as explained after, during amputations of the blood vessel, the both side walls in longitudinal direction of the blood vessel are fused at the amputated portion of the blood vessel. Then, the side walls are connected to each other so as to make two ends, which are opposed at the amputated portion. As a result, bleeding is prevented by the two ends and the tying of the blood vessel is not required.

In the present invention, a laser light reflecting layer can be formed on each laser light transmissive probe at its side face opposite to the other side face of the other probe. Thus, the laser light can be emitted from the other probe-side face concentratedly.

Laser light scattering means can be provided on the laser light emitting portion of each laser light transmissive probe. In this case, the laser light can be irradiated efficiently against the target area of the tissues.

A holder can be provided in this apparatus. This holder can hold the opposed pair of laser light transmissive probes and is operated by a medial operator so that the opposed pair of fore end portions are brought into or out of contact with each other. By means of this holder, the opposed pair of transmissive probes can be operated like a pincette so as to be in contact with or separated from each other corresponding to the movement of the pair of fore end portions of the holder.

The laser light transmitting system, such as an opposed pair of optical fibers, can be set in the opposed pair of fore end portions of the holder respectively. Thus, damage to the laser light transmitting system can be prevented.

The opposed pair of laser light transmissive probes are bent inwardly so that when their fore end portions are brought into contact with each other, a space is formed so as to be encircled by them. Then, the opposed pair of laser light emitting portions are formed on at least their base-side portions at the peripheral portion of the space adjacent to their contacting portion. By utilizing this structure of the probes instead of a conventional electrical snare, a projected tumor can be excised easily by pulling the probes toward the medical operator while they are closed or contact each other.

Means for detecting a temperature of the target area of the tissues is preferably provided. Thus, the medical operation can be carried out under exact temperature control. Therefore, this means can be utilized efficiently for anastomosis of the tissues and thermal therapy for cancer tissues, because they particularly require precise temperature control.

A sensor detecting a temperature can be attached to one or both of the opposed pair of laser light transmissive probes so as to contact them. From a detected temperature obtained by this sensor, a temperature at a position of other than the position the sensor can be estimated because there is a determined relation between the two temperatures. In the medical operation, the light transmissive probes are brought into contact with the target area of the tissues and a temperature of the target area is required. By using this sensor, this required target temperature can be estimated easily from the detected temperature.

Since the laser light transmissive probe is normally fabricated from heat resistant ceramics, it is weak against a shock. At least a portion of the peripheral face of the light transmissive probe can be covered with a protective material. This protective material has a strength higher than the strength of the light transmissive probe against the shock. Consequently, when the probe receives a shock, its damage can be reduced by the protective material.

It is difficult to form the laser light reflecting layer on the laser light transmissive probe directly. However, the reflecting layer is formed easily on the internal peripheral face of the protective material such as the metal material.

On the other hand, means for aspirating the target area of the tissues is preferably provided between the opposed pair of laser light transmissive probes. In this case, the target area of the tissues can be pulled up by aspirating. Therefore, the anastomosis, the amputations, the excisions and the thermal therapy for the target area can be performed precisely and easily.

Means for detecting the tissue temperature is preferably provided on the above mentioned means for aspirating. With this structure, the temperature of the target area of the tissues can be detected directly during the aspiration of the tissues.

If each emitting face is formed on the other probe-side face of each laser light transmissive probe and at least one portion of the emitting face is planar, a broad target area of the tissues can be pinched by the opposed pair of laser light transmissive probes.

If just a single impinging means is provided for each laser light transmissive probe, the laser light may not be transmitted to the probe efficiently. Therefore, a plural number of laser light impinging means are preferably fixed to each laser light transmissive probe which is, for example, plane-shaped. Thus, the laser light can be transmitted to the inner side of the probes efficiently.

Means for injecting a fluid under pressure against the target area of the tissues can be provided between the opposed pair of laser light penetrating probes. During the medical operation, pieces of living tissues and blood are splashed and may become attached to the light transmissive probes. However, this situation can be eliminated using means for injecting a fluid against the target area.

Apparatus of the present invention can be used not only in a surgical field but also in an internal medical field. In the internal medical field, one preferable example is as follows: The holder is Y-shaped. Then, each of the opposed pair of laser light penetrating probes are fixed to the one of tip ends of the branch (V-shaped) portion of the holder, respectively. Further, the branch portion of the holder has flexibility. Then, the holder is inserted in a sheath tube so that the tip ends project upwards and the base portion projects downwards from the sheath tube and are each exposed. Thus, the holder can be moved along the sheath tube corresponding to the pushing and pulling operation of the base portion by the operator. When the holder is pushed, its branch portion is spread so that both divided portions consisting of the branch portion are apart from each other. On the other hand, when the holder is pulled, its branch is closed. Due to the above structure, this apparatus can be utilized in medical operations for visceras such as a stomach and the like. In this case, first, an endoscope is inserted into a hole of a body. Next, this apparatus is inserted along the hole. Then, by pushing the holder, the opposed pair of light transmissive probes, which are put in the both divided portions respectively, are spread so as to be apart from each other. Further, when the laser light is irradiated against the target area, the holder is pulled so that the opposed pair of light transmissive probes move inward toward each other. Thus, the target area of the tissues can be brought into contact with the opposed pair of probes from its both sides. These operations, performed while the movement of apparatus in the body, can be observed through an endoscope.

THE BEST MODE TO CARRY OUT THE INVENTION

Figure 1:
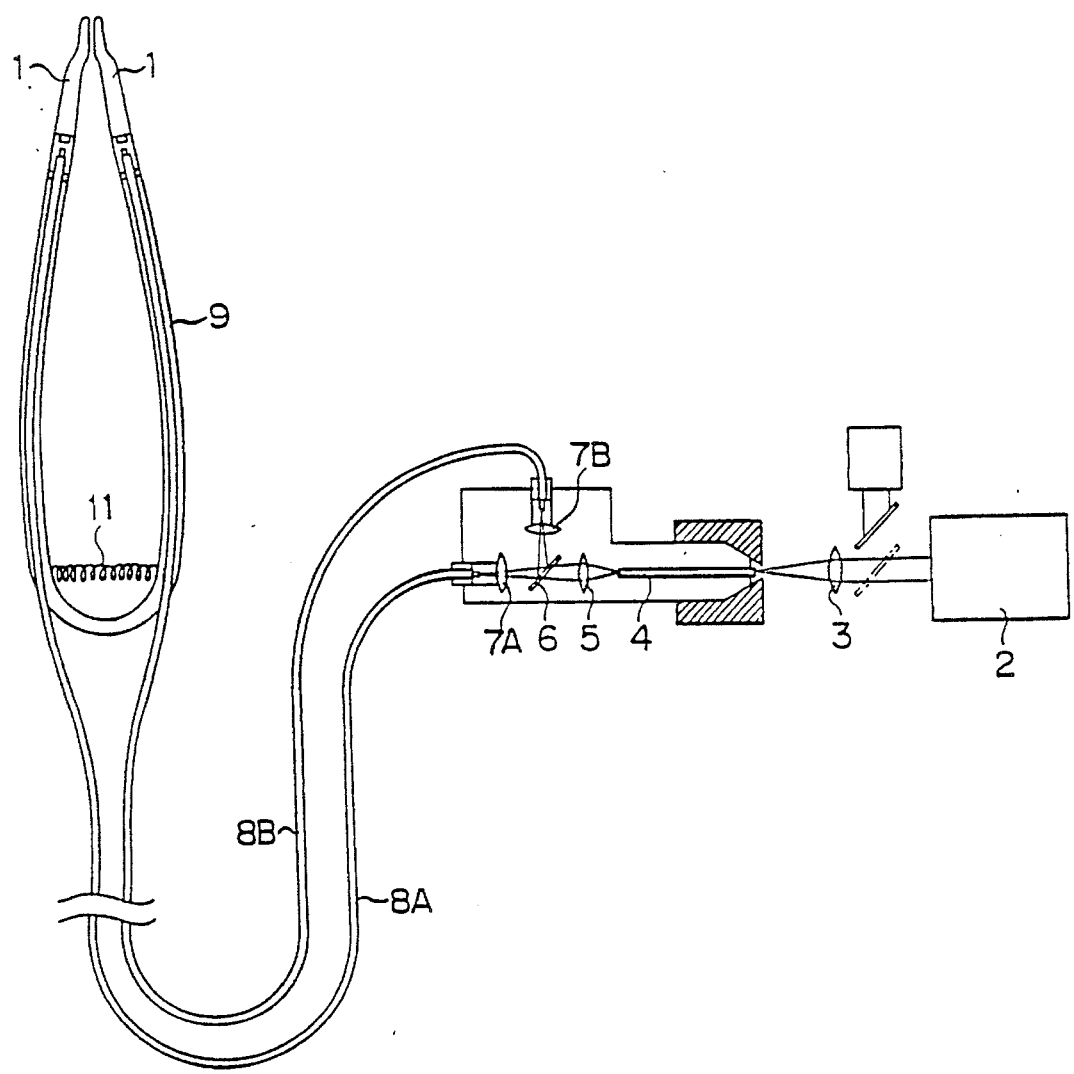
FIG. 1 is a schematic illustration showing an entire apparatus or system for a medical treatment related to the present invention.

Now, the present invention is described more particularly referring to the drawings.

FIG. 1 shows the whole of one embodiment of an apparatus for a medical treatment in accord with the present invention. Laser light is emitted from a laser light generator 2 and transmitted through a laser light transmitting system explained later. Then, the laser light impinges onto the proximal end of each of an opposed pair of laser light transmissive probes 1, 1. The laser light transmissive probes 1, 1 are disposed to be opposed each other. The laser light is emitted from areas of the probes 1,1 at or near the distal ends thereof, to irradiate the target area of tissues.

In the laser light transmitting system, the laser light travels as follows;

The laser light emitted from the laser light generator 2 goes through a lens 3 and impinges onto an optical fiber 4. Next, the laser light is emitted from the fore end of the optical fiber 4 and goes through a lens 5. Then, the laser light is divided into two portions by a 50/50% spectral mirror 6.

The divided portions of the laser light impinge onto optical fibers 8A, 8B through lenses 7A, 7B respectively. The optical fibers 8A, 8B are covered with protective tubes respectively. Further, the fore end portions of tho optical fibers 8A, 8B are provided in a U-shaped holder, in this embodiment a pinching holder 9. The pinching holder 9 is made of metal and moves like a pincette. The above mentioned opposed pair of laser light transmissive probes 1, 1 are supported integrally by the fore end portions of the pinching holder 9.

Figure 2:
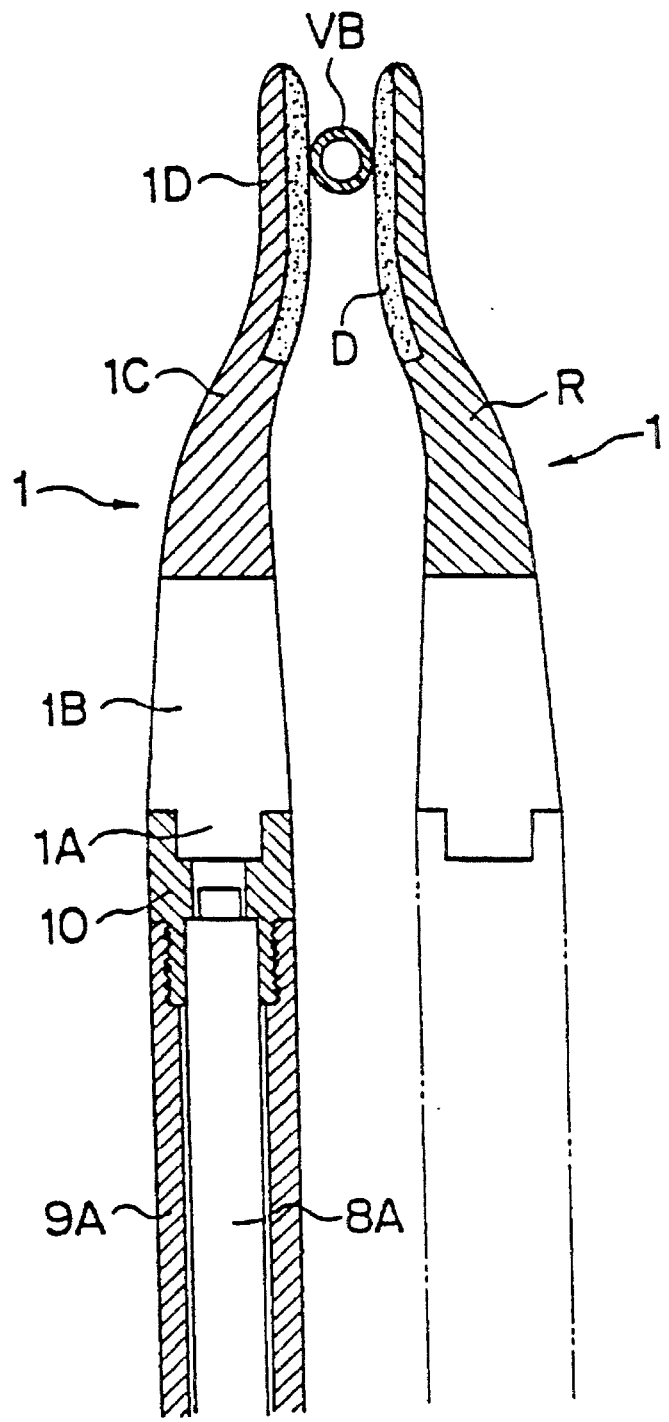
FIG. 2 is a plan view, partly in cross section, of the laser light emitting portion of the apparatus shown in FIG. 1.

The opposed pair of probes 1, 1 are supported, for example, in a manner shown in FIG. 2. The probe 1 is supported by the pinching holder 9 and optically connected to the optical fiber 8A. Referring to the left side of FIG. 2, it is clear that a holder-cylinder 9A is connected to the probe 1 through a connector 10 so that the optical fiber 8A can be disposed so as to be apart from the base-side impinging surface at the proximal end of the probe 1. In FIG. 2, only the left side of the holder 9 is shown. However, the right side laser light transmissive probe 1 is supported by the pinching holder 9 and optically connected to the optical fiber 8B in the same way. The holder 9 is fabricated from a flexible material. Alternately, a resilient spring 11 is provided on the base portion of the holder 9 so that the fore end portions of the holder 9 can be moved freely so as to be closed and moved apart from each other corresponding to the operation of the medical operator.

Now, first embodiment of the opposed pair of laser light transmissive probes 1, 1 are explained closely referring to FIGS. 2 to 8.

The laser light transmissive probe 1 is fabricated from a heat resistant ceramic, such as quartz. A smaller radius side portion 1A is formed at the base proximal end of the probe 1 and is engaged in the connector 10. A conical portion 1B is formed at the base portion so as to be slanting gently and continuously to the smaller radius side portion 1A. The smaller radius side portion 1A and the conical portion 1B are supported by the holder 9 coaxially with the optical fiber 8A. The axis of the smaller radius side portion 1A and the conical portion 1B is substantially the same as the axis of the laser light impinging on the proximal end of the probe from the optical fiber proximal.

A portion of each laser light transmissive probe 1 is bent toward the corresponding portion of opposite laser light transmissive probe 1 so as to form a bending portion 1C. Then, a parallel portion 1D is formed at the distal end portion of the laser light transmissive probe 1 so as to be continuous to the bending portion 1C. The ridge line of the parallel portion 1D is parallel to the above mentioned axis of the base portion of the laser light transmissive probe 1.

Figure 3:
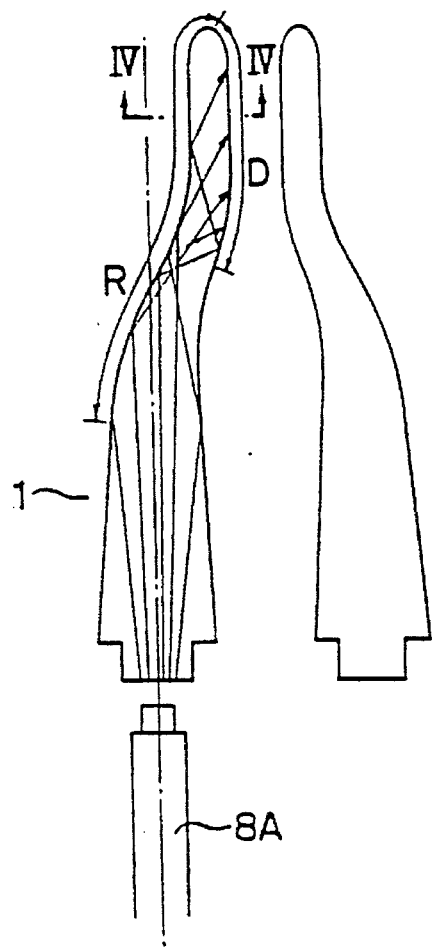
FIG. 3 is an illustration showing laser light transmission paths.
Figure 4:
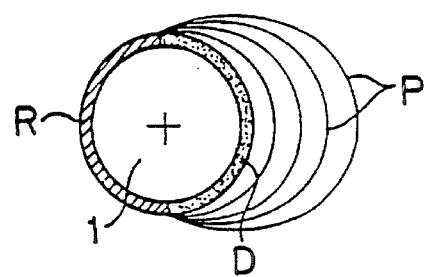
FIG. 4 is cross sectional view taken on line IV—IV of FIG. 3.
Figure 5:
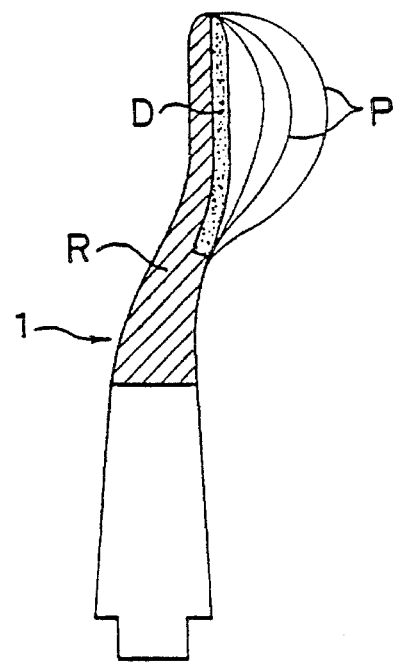
FIG. 5 is an illustration showing a power density distribution of laser light emission.

On the other hand, as shown in FIGS. 2 and 3, a laser light scattering layer D is formed at the internal side face of the parallel portion 1D. In other words, the scattering layer D is formed on another probe-side face which is directly opposite the other laser light transmissive probe 1. In FIG. 2, this scattering layer D is illustrated by marking dots. Referring to FIG. 3 showing paths of laser light reflection, in this embodiment, at a portion of the conical portion 1B, bending portion 1C and the parallel portion 1D other than the scattering layer D, the laser light is reflected. Therefore, in each laser light transmissive probe 1, a laser light reflecting layer R is formed at the surfaces of the above mentioned portions where the laser light is reflected. In FIG. 2, the reflecting layer R is shown by hatching.

For forming the reflecting layer R, a gold plated layer or aluminum plated layer is coated on the surface of the laser light transmissive probe 1.

Figure 6:
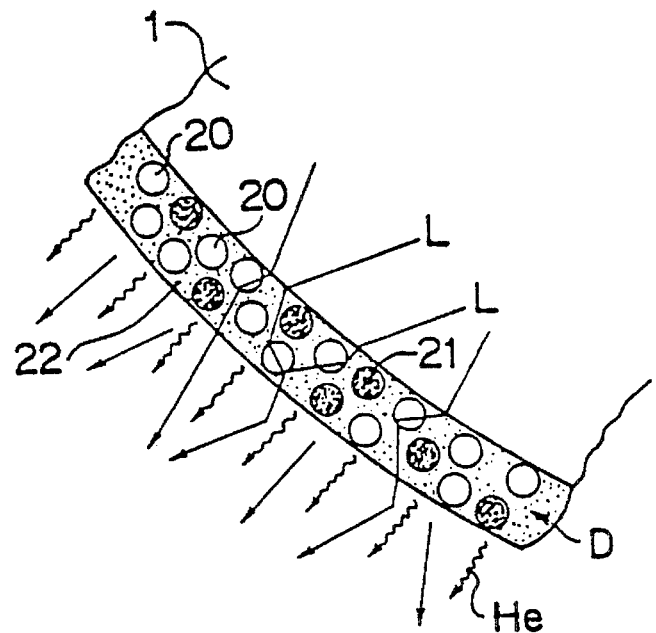
FIGS. 6 and 7 are schematic enlarged sectional views showing embodiments of scattering layers which may be applied to light emitting surfaces of the probes in the present invention.
Figure 7:
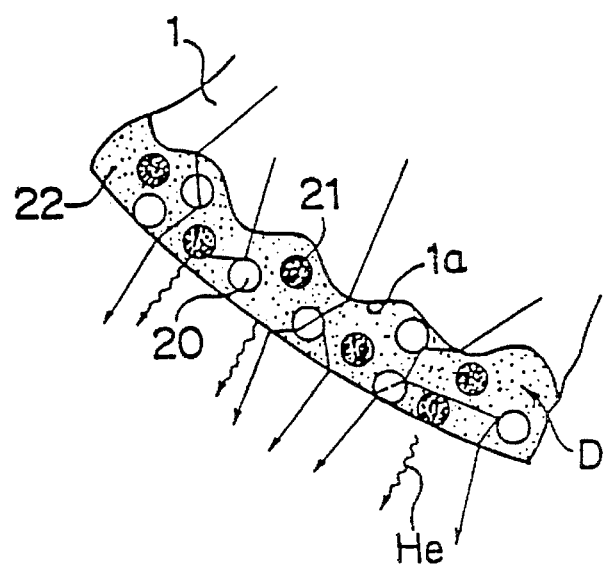

The laser light scattering layer D can be formed by just roughening the surface of the laser light transmissive probe 1. Alternately, in order to give a larger scattering effect, as shown in FIG. 6, the scattering layer D preferably contains scattering particles 20 and absorbing particles 21 of the laser light L and a binder 22, into which transmissible particles of laser light L are melted. Further, as shown in FIG. 7, the scattering layer D can be formed on a rough surface 1a of the laser light transmissive probe 1 to give a still larger scattering effect.

As explained before, the material of the laser light transmissive probe 1 of the present invention is preferably ceramics, such as artificial and natural diamond, sapphire, quartz and the like, because of their high heat resistance.

For the laser light scattering particles, a material, which has a larger refractive index for the laser light than that of the laser light transmissive probe, is used. For example, there are natural or artificial materials such as diamond, sapphire, quartz (it preferably has a high melting point), single crystal zirconium oxide ($Zr_2O_3$), glass having a high melting point, laser light transmissive synthetic resin having heat resistance and a laser light reflective metal such as gold, aluminum and the like. Alternatively, the material of the laser light scattering particles can be metal particles, which is laser light transmissive or not and whose surface is coated by a laser light reflective metal (gold, aluminum or the like) by means of a surface treatment such as plating and the like.

The material forming the binder is preferably made from the laser light transmissive particle which can make a film when it melts and more preferably which has heat resistance, such as natural or artificial, sapphire, quartz, glass, transmissible and heat resistant synthetic resin and the like. A suitable transmissive binder material is selected from these materials in consideration of the relation to the material of the laser light transmissive probe 1.

The laser light absorbing particles are carbon, graphite, iron oxide, manganese dioxide or any other materials which can absorb the laser light to generate heat energy.

A content of each type particle in the laser light scattering layer (wt %) and each average particle size is preferably within ranges as shown in a following table. More preferable content and particle size are shown in parentheses.

|  | Content (wt %) | Average Particle Size (μm) |
| --- | --- | --- |
| Scattering Particle | 90–1 (70–20) | 0.2–300 (1–50) |
| Transmissible Particle | 10–90 (20–50) | 0.2–500 |
| Absorbing Particle | 90–1 (70–10) | 0.2–500 (1–100) |

The thickness of the laser light scattering layer is preferably 10 μm–5 mm, more preferably 30 μm–1 mm. The scattering layer is formed as explained hereinafter. If the scattering layer having a desired thickness can not be formed by one cycle of the method, the method should be repeated until the layer having the desired thickness can be obtained.

The above mentioned three kinds of particles are dispersed in a dispersion medium, which then is heated to a temperature is higher than the melting point of the transmissive particle. Then an uncoated probe is dipped in the heated dispersion.

Alternatively, the three kinds of particles are melted and sprayed onto the uncoated probe.

Further, other suitable methods for forming the scattering layer can be used.

By the above described first method, the dispersion containing the three kinds of particles can be painted on the uncoated probe. Moreover, this painting method facilitates the coating operation because only a part of the probe which is desired to be covered with the laser light scattering layer is dipped in the dispersion.

As the dispersion medium, a suitable liquid such as water, alcohol or mixture thereof can be used. Further sugar or starch is added to increase the viscosity of the dispersion medium.

As described before, according to the present invention, by forming the laser light scattering layer D as well as laser light reflecting layer R, the laser light can be concentrated on the scattering layer D. Accordingly, as shown by power density distribution curves P in FIGS. 4 and 5, the laser light can be irradiated concentratedly against the target area of the tissues from only the scattering layer D.

Now, this laser light scattering will be explained in more detail. As laser light L emitted from the laser light transmissive probe 1 passes through the laser light scattering layer D, the laser light L impinges on each laser light scattering particle 20 in the scattering layer D to be partially reflected on the surface of the scattering particle 20, or to partially penetrate into and emerge again from the particle 20 with refraction. Therefore, the laser light L is emitted in various directions over the whole external surface of the scattering layer D. This produces the large area of the laser light irradiation.

Further, the scattering layer D preferably contains the laser light absorbing particles 21 made of carbon and the like. In this case, when the laser light L impinges on each laser light absorbing particles 21, the greater part of the energy of the laser light L is converted to heat energy He by means of the laser light absorbing particles 21, and the tissues are heated by the heat energy from the scattering layer D.

Thus, as vaporization of the tissues is accelerated, the tissues can be incised with a low energy of the laser light L impinged onto the laser light transmissive probe 1. Therefore, when tile tissues are incised, the laser light transmissive probe 1 can be moved quickly. Accordingly, the medical treatment can be carded out in short time. Further, since a high power level of the laser light L is not required, the medical treatment can be carded out with a relatively cheap and small scaled laser light generator.

On the other hand, if a dispersion containing the above mentioned laser light absorbing particles and the light scattering particles is coated on the surface of the laser light transmissive probe 1, after evaporation of the dispersion medium, the contact of the probe with the tissues or other substances causes a damage to the scattering layer. Because both particles are attached to the surface of the laser light probe only by physical adsorptive power. Therefore, use of the binder which bonds the laser light absorbing particles and the light scattering particles to the surface of the laser light transmissive probe improves adhesion of the scattering layer to the probe is enhanced.

FIG. 3 shows the paths of the laser light reflection in the laser light transmissive probe 1. As shown in FIG. 3, the laser light is concentrated on the laser light scattering layer D, while the laser light is reflected in the probe 1. Further, FIG. 3 shows that the probe 1 has a shape suitable for the above described laser light reflection. In the present invention, the scattering layer D is not necessary. However, if the scattering layer D is not provided, the graph of the laser light power density distribution of FIG. 4 will be projected toward the fight sharply. In this case, the probe can be mainly used for only incisions with a lower ability in hemostasis, as compared to the probe having the scattering layer D. Additionally, the graph of the laser light power density distribution of FIG. 5 will project sharply toward the fight side of the upper portion. This situation can be estimated from the angle of laser light emission shown in FIG. 3. In this case, the transmissive probe 1 can be used for the amputation of only thin blood vessels and the like.

A laser light emitting portion, on which the laser light scattering layer D is formed, and a length of 2–10 mm, preferably has a length of 3–7 mm.

Apparatus for the medical treatment related to the present invention is used by a medical operator in a way explained as follows.

First, the power switch is put on. Next, as shown in FIG. 2, with the holder 9 controlled by the medical operator, the opposing pair of laser light transmissive probes 1, 1 are located so that the target area of the tissues are disposed between the pair of probes 1, 1. In this embodiment, the probes 1, 1 are disposed at the both sides of the blood vessel BV respectively. Next, a switch 12 of FIG. 1 is put on. A hand switch (not shown) is provided on the holder 9 to activate the switch 12.

Figure 8:
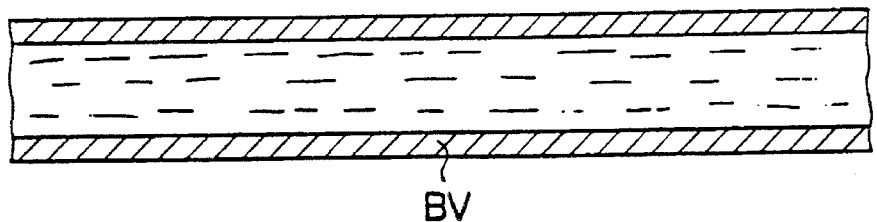
FIGS. 8 to 10 are cross sectional views showing a process of an amputation for a blood vessel.
Figure 9:
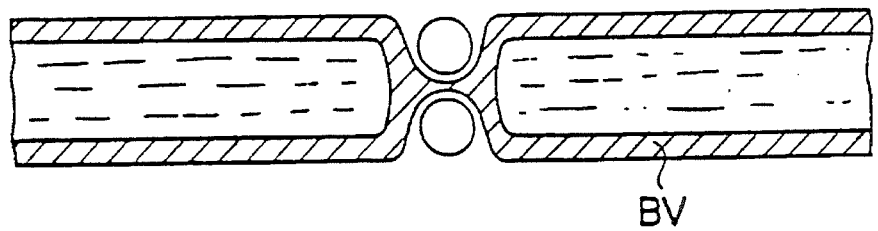
Figure 10:
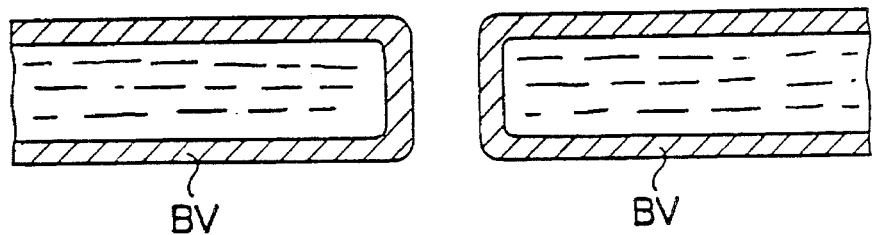

By controlling the hand switch, the laser light is irradiated from the laser light scattering layers D, D against the blood vessel BV. As shown in FIG. 8, first, a blood vessel BV has an original shape. Then, during the amputation using the laser light transmissive probes 1, 1, the walls of the blood vessel BV are melted by the laser light irradiation. As shown in FIG. 9, the walls of the blood vessel BV are fused between the laser light transmissive probes to form a connecting portion. Accordingly, blood can not flow at the connecting portion. Further, since the laser light is irradiated against the connecting portion, as shown in FIG. 10, the blood vessel is amputated. In this amputation, bleeding is prevented at the end portions of the both amputated blood vessels.

When the conventional laser light emitting probes are used, comparing incisions with a mechanical knife, bleeding is prevented well. However, the bleeding is still caused to some degree. On the other hand, with apparatus of the present invention, even if hemorrhagic tissues such as liver are treated, the bleeding is substantially eliminated.

The inventor certified from many experiments of the medical operations that the laser light irradiation has an ability in hemostasis. However, in amputation, with the conventional laser probes, this hemostasis is shown in only cases of capillaries and blood vessels having diameters smaller than 1.5 mm. When the blood vessels having diameters being larger than 1.5 mm are amputated with the laser probes, the bleeding can not be prevented.

The reason is not known closely why the thick blood vessel can be amputated with the opposed pair of laser light penetrating probes without bleeding. However, it can be estimated as follows.

First, the laser light is emitted from the opposed pair of laser light transmissive probes 1, 1, while heat is produced so as to melt the walls of the blood vessel BV. At the same time, the blood vessel BV is pinched by the opposed pair of probes 1, 1. Then, the walls are fused to each other to produce the connecting portion which serves as a partition preventing the blood from flowing. Further, it can be thought that anastomosis is also performed during the amputation.

Practically, the inventor confirms that arteries having diameters of about 6 mm can be amputated with the laser light transmissive probes of the present invention without bleeding, by controlling the laser light emitting power.

Apparatus for the medical treatment of the present invention can be used without bleeding in amputations and incisions of a blood vessel, a bile duct, a uterine tube and an alimentary canal and in the incision of internal organs such as the liver and the like. Additionally, it can be used in coagulation, anastomosis, and vaporization. Using the present invention, for a normal medical operation, the power level of the supplied laser light is smaller than 10 W. Further, medical operations can be carried out with a power level smaller than 5 W.

YAG laser light generally can be used as the laser light in the present invention. However, other laser light, such as argon laser light and the like can be used.

Figure 11:
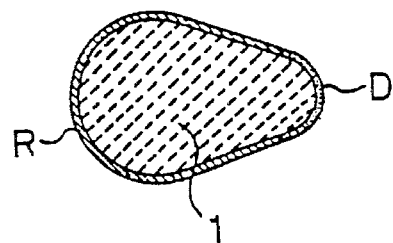
FIGS. 11 to 13 are transverse cross sectional views of three kinds of laser light transmissive probes.
Figure 12:
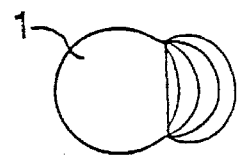
Figure 13:
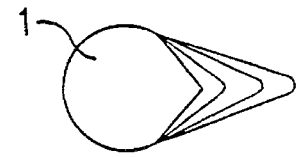

In the present invention, when the medical operation is performed mainly for coagulation, as explained before, the cross section of the laser light transmissive probe 1 is preferably a circle. However, when the medical operation consists mainly of incisions and amputations, the suitable cross section of the laser light transmissive probe 1 is an angular shape. For example, FIG. 11 shows an angular cross sectional shape of the probe with a projection at the emitting portion-side, and FIG. 13 shows another angular cross sectional shape of the probe with an even sharper projection. Alternately, as shown in FIG. 12, when the medical operation is performed mainly for pinching coagulation against the target area having a long distance, the laser light emitting portion can be flat. Thus, the cross section of the laser light transmissive probe 1 is not limited to a certain shape.

Figure 14:
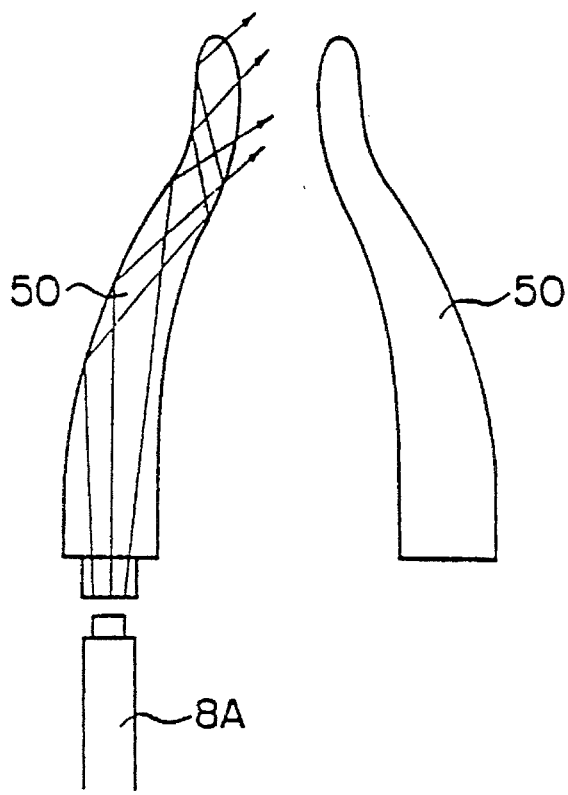
FIGS. 14 to 16 are illustrations showing other embodiments of opposed pairs of laser light transmissive probes.

FIG. 14 shows another laser light transmissive probe 50 which has another different shape and the paths of the laser light reflection within one such probe. As clearly shown in FIG. 14, the laser light can reach the laser light emitting portion with single reflection.

Figure 15:
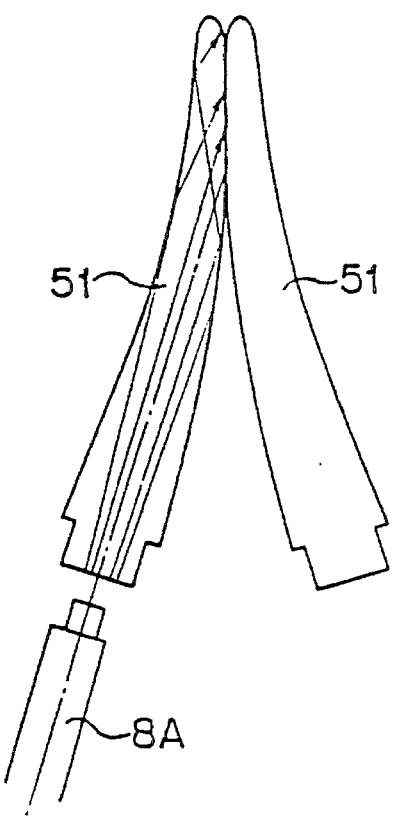

FIG. 15 shows another laser light transmissive probe 51 which has still another shape and whose fore end portion is bent backward. In this case, the laser light can reach directly at the laser light emitting portion while there is substantially no laser light reflection.

Figure 16:
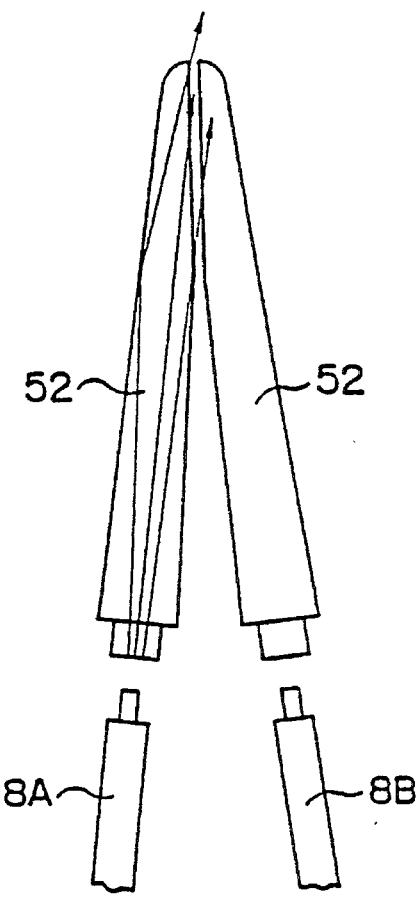

FIG. 16 shows a modified embodiment of the laser light transmissive probe. In this embodiment, the conical portions of the opposed pair of probes are cut away so as to have the cross sections of FIG. 12. Also in this case, the number of internal reflections of laser light is not so great.

In the embodiments of FIGS. 14 to 16, the laser light reflection layer R and the laser light scattering layer D are preferably formed, although they are not shown in these figures. As explained in the above description of the first embodiment, the more the laser light is reflected in the laser light transmissive probe, the more laser light can reach the laser light emitting portions. Therefore, by provision of the reflection layer R and the scattering layer D, high power level of laser light supplied to the probe is not required.

Figure 17:
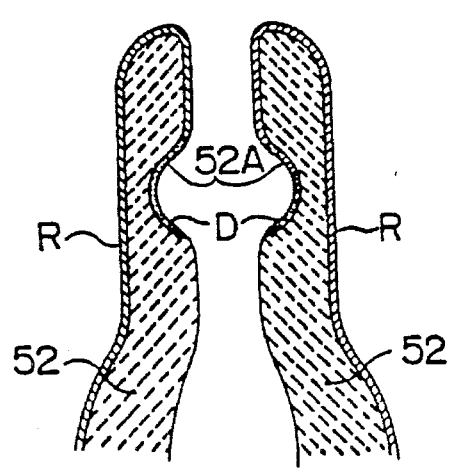
FIG. 17 is a longitudinal cross sectional view showing an important part of still another opposed pair of laser light transmissive probes.
Figure 18:
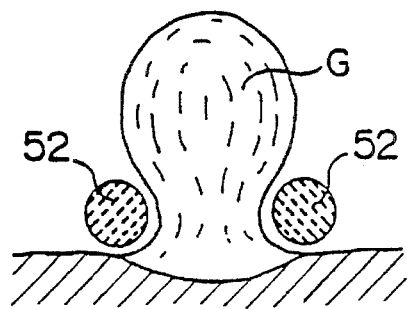
FIG. 18 is an illustration showing an embodiment of excision of a projected tumor.

On the other hand, as shown in FIGS. 17 and 18, when a projected tumor G formed on the surface of the tissues are excised, an opposed pair of laser light transmissive probes 52, 52 provided with pair of constrictions 52A, 52A can be used effectively. The opposed pair of laser light scattering layers D, D are preferably formed on the inner surface of the opposed pair of constrictions 52A, 52A respectively.

Figure 19:
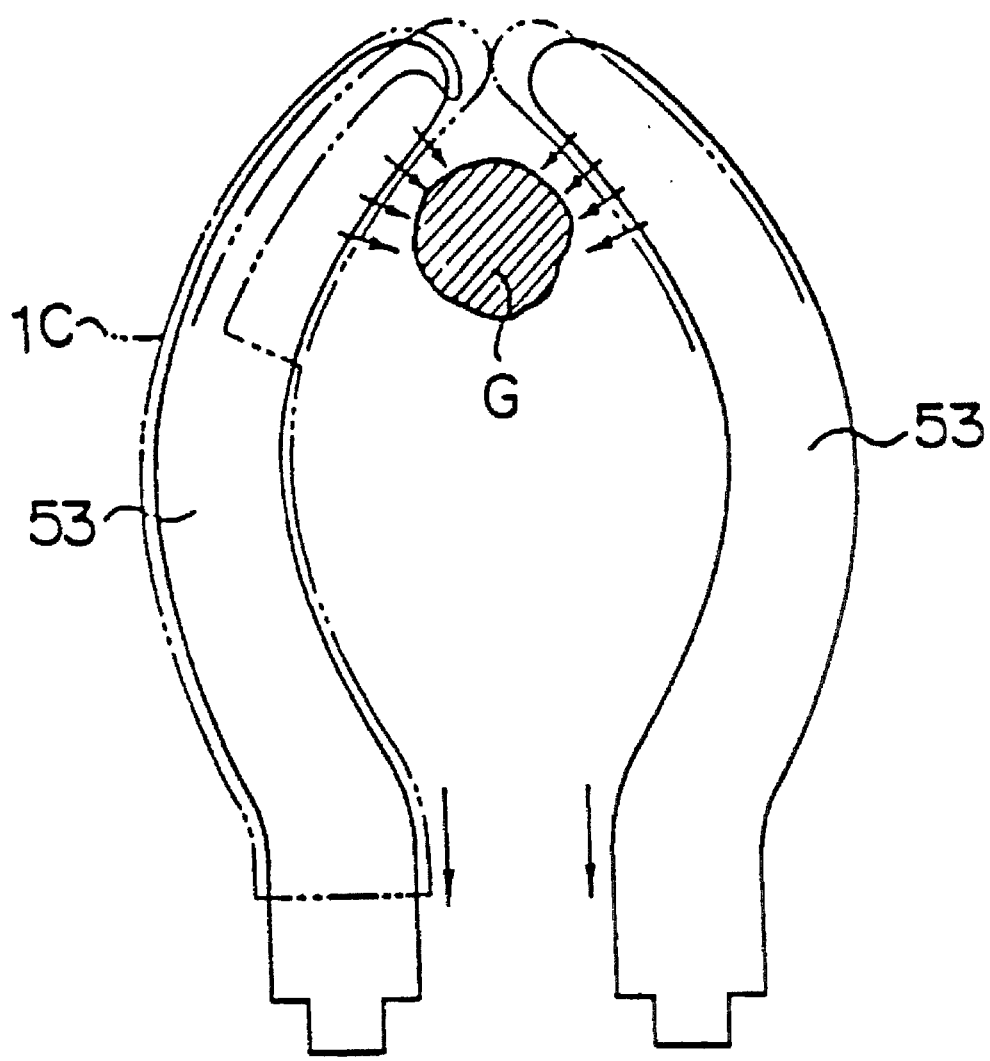
FIG. 19 is a schematic illustration showing an important part of another opposed pair of laser light transmissive probes.

For excision of the projected tumor G, as shown in FIG. 19, the opposed pair of laser light transmissive probes 53, 53 are bent inwardly so that their fore end portions are brought into contact with each other (this condition is shown by imagine lines). Thus, a ring-shaped space encircled by them can be formed. Then, the laser light emitting portions are formed on at least the base-side portions of the opposed pair of probes 53, 53 at the peripheral portion of the ting-shaped space adjacent to their contacting portion respectively. Thus, the root of the projected tumor G can be excised easily by pulling the opposed pair of laser light transmissive probes 53, 53 in the direction indicated by the arrows shown in this figure.

Apparatus of the present invention can be utilized efficiently for not only the above mentioned amputation and incision but also for the anastomosis of the tissues, the thermal therapy for cancer tissues, the coagulation and the vaporization. Particularly, in case of the anastomosis and the thermal therapy, means for detecting a temperature of the target area of the tissues is preferably provided. In each medical treatment, the temperature of the tissues should be controlled. The suitable temperature depends on the kind of tissues treated. However, it can be determined generally in each treatment. For example, the medical operation for the anastomosis can be carded out at the temperature of 60° to 80° C. On the other hand, the thermal therapy can be carried out at the temperature of 42° to 45° C. For detecting the temperature, a contact type sensor such as a thermocouple or non-contact type device such as an optical sensor means can be used.

Figure 20:
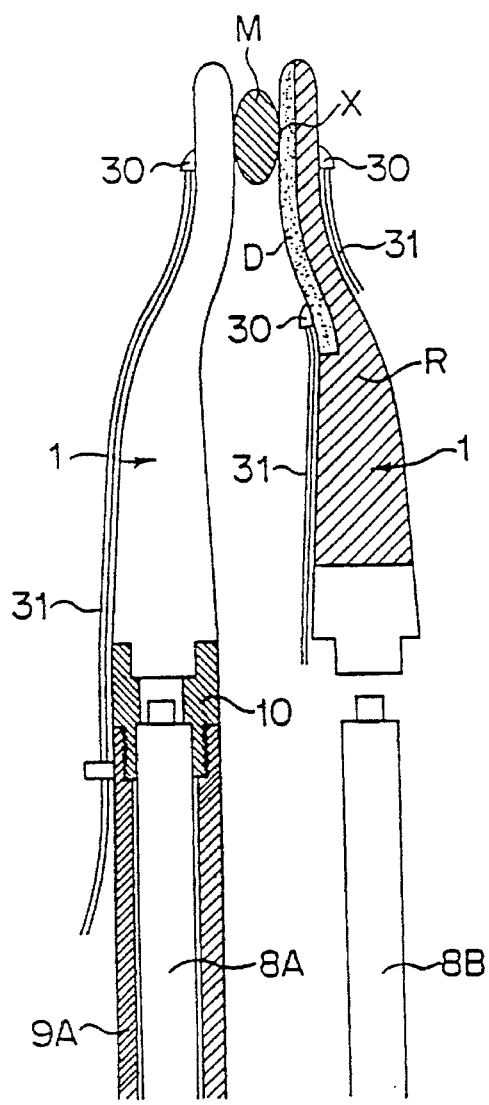
FIG. 20 is an illustration showing an embodiment with sensors for detecting a temperature provided on an opposed pair of laser light transmissive probes.

FIG. 20 shows the opposed pair of laser light transmissive probes 1, 1 having sensors 30, 30 detecting the temperature. Each sensor 30 consists of the thermocouple and is mounted in contact with the back or inner surface of each light transmissive probe 1. Each of wires 31 connected to each sensor 30 can be supported by means of the holder 9A or the like.

Figure 21:
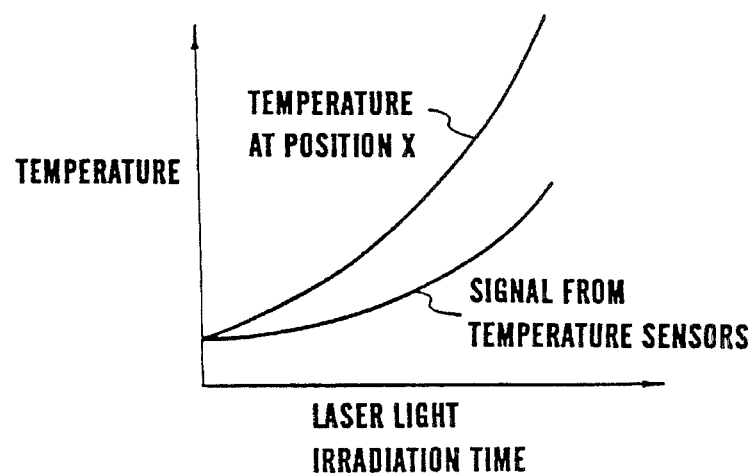
FIG. 21 is a graph showing the relationship of the temperature of tissues at a position where a sensor detecting the temperature is inserted and the temperature of the tissues at another position.

A detected temperature obtained by this sensor 30 is different from the temperature of the surface of the target area of the tissues such as that of cancer tissues M. However, as shown in FIG. 21, the temperature of the position X of the tissues M brought into contact with the laser light transmissive probe 1 and the detected temperature obtained by the sensor 30 have a determined relationship. Therefore, according to this relationship, by correcting the detected temperature obtained by the sensor 30, the temperature of the position X at the point of contact with tissue M can be estimated.

Figure 22:
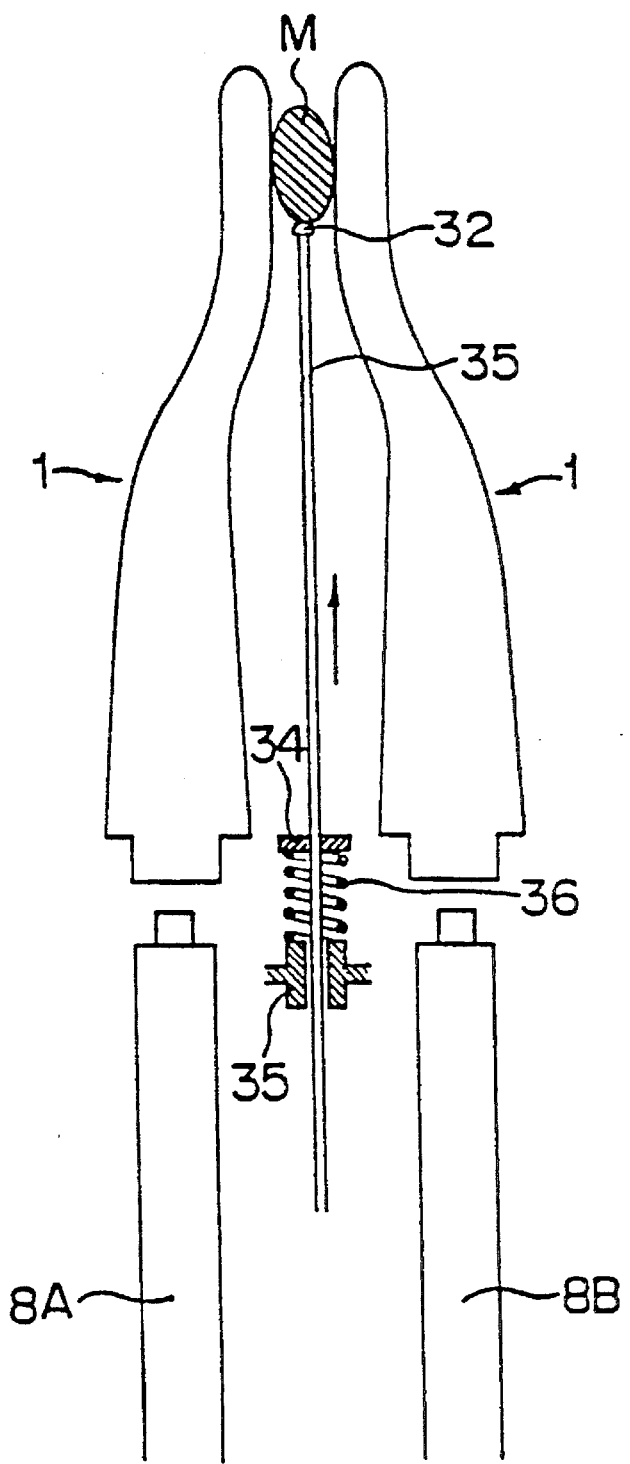
FIGS. 22 and 23 are illustrations showing other embodiments of sensors for detecting temperatures provided on opposed pairs of laser light transmissive probes.

FIG. 22 shows the opposed pair of laser light transmissive probes 1, 1 having another sensor 32 detecting the temperature, which is brought directly into contact with the target area of the tissues, such as the blood vessel BV. Accordingly, in this embodiment, the temperature of the target area can be detected directly. The sensor 32 is fixed to the fore end portion of a moving rod 33. A flange 34 is fixed at a suitable position of the rod 35. A spring seat 35 is fixed to the holder 9 so that the rod 35 can go through the spring seat 35 (the relational construction of the spring seat 35 and the holder 9 is not shown in this figure). Then, a resilient spring 36 is provided between the flange 34 and the spring seat 35.

This sensor 32 is used to detect the temperature of the target area of the tissues M during the laser light irradiation. First, the tissues M are pinched by the opposed pair of laser light penetrating probes 1, 1. Next, the moving rod 33, which has been pulled, is pushed toward the tissues M by means of the spring 36 so that the sensor 32 contacts the tissues M. Then, the laser light is irradiated against the tissues M by the opposed pair of probes 1, 1, while the temperature of the tissues M is detected directly by the sensor 32.

Figure 23:
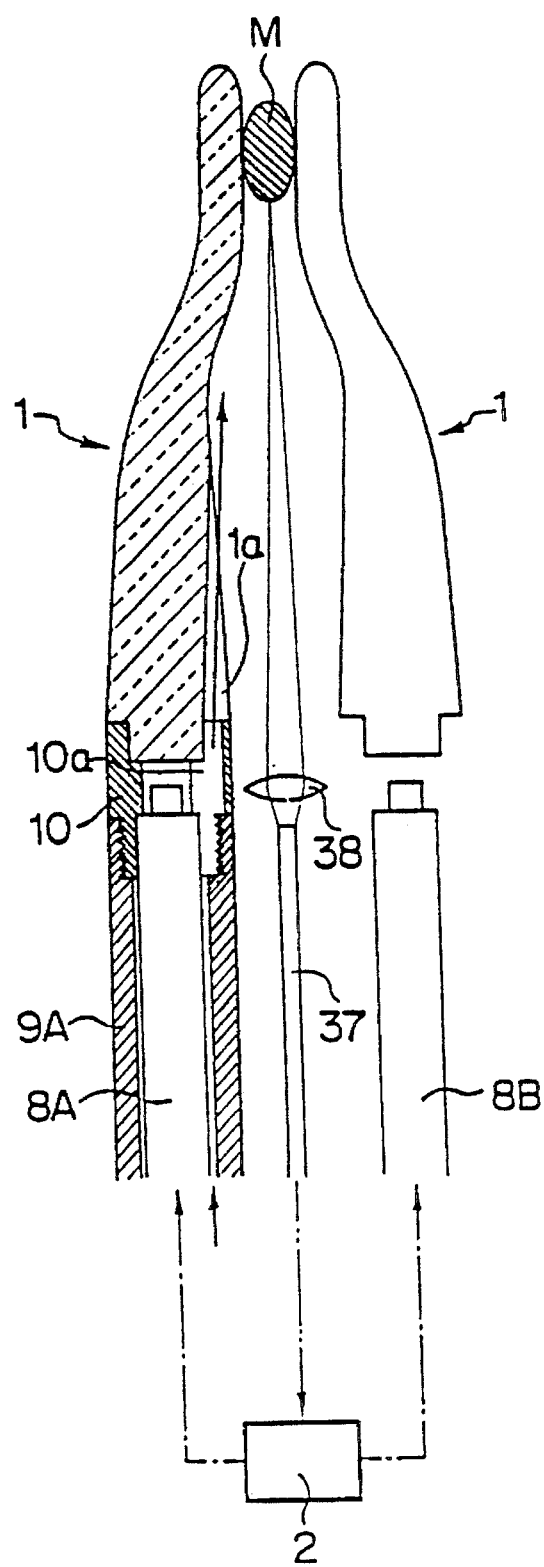

FIG. 23 shows a non-contact type of sensor detecting the temperature of the tissues M optically. In this case, laser light is irradiated against the tissues M from a optical fiber 37 through a lens system 38. At the same time, the power level of the laser light emitted from the surface of the tissues M is detected. Thereby, the temperature of the surface of the tissues M can be known. During this detecting, as shown in FIG. 22, the power level of the laser light impinged onto the opposed pair of laser light transmissive probes 1, 1 from the laser light generator 2 can be controlled on the basis of a signal showing the detected temperature.

The laser light irradiation against the tissues during the medical operation may cause pieces of tissues, blood and the like to splash on and/or become attached to the surfaces of the opposed pair of laser light transmissive probes 1, 1. In this case, the opposed pair of transmissive probes 1, I should be treated so as not to be damaged by this splash. Also, in many cases, the tissues M should be cooled. Accordingly, apparatus of the present invention preferably has means for directing a flow of air, physiological saline solution or the like at the target area of the tissues M. By this means, the tissues can be cooled and the pieces of tissues and blood attached to the opposed pair of probes 1, 1 are washed away. The construction of this means is explained in more detail below. For example, as shown in FIG. 23, a path of the air, physiological saline solution or the like is formed. This path consists of a gap formed between the holder-cylinder 9A and the optical fiber 8A, hollow space 10a formed at one side of the connector 10 and a notch 1a formed at the one corner of the penetrating probe 1. The air, physiological saline solution or the like is supplied through the path so as to be ejected against the target area of the tissues M.

As explained before, the laser light transmissive probe 1 is fabricated from ceramics. The strength of the probe 1 depends on the kind of material. However, in many cases, the light transmissive probe maybe broken by a shock caused by being brought into contact with other substances. Therefore, at least one portion of the peripheral surface of the laser light transmissive probe 1 is preferably covered with a protective material having high strength against the above mentioned shock.

Figure 24:
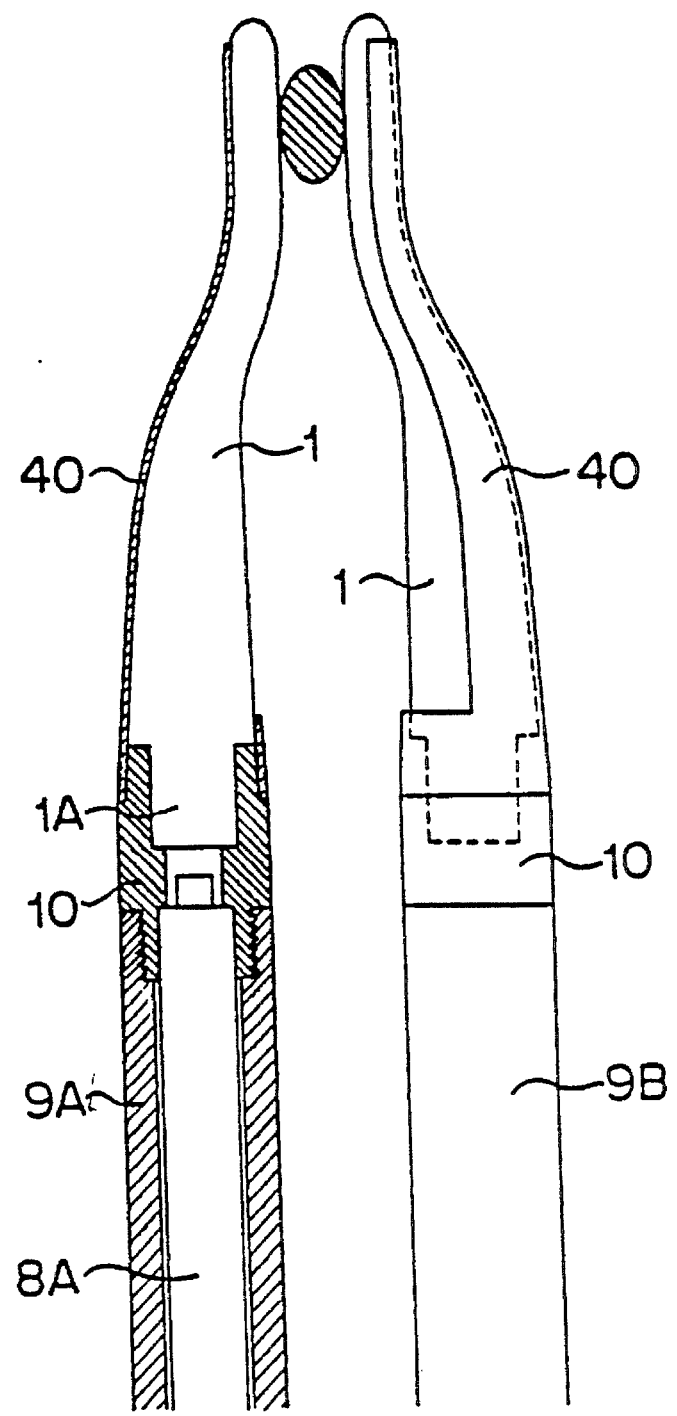
FIG. 24 is a longitudinal cross sectional view showing an opposed pair of laser light transmissive probes on which protective means formed of a protective material is provided.
Figure 25:
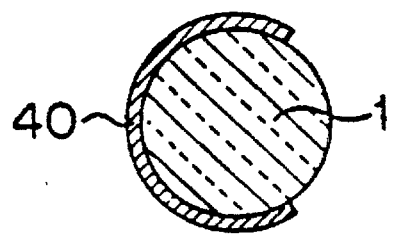
FIGS. 25 to 27 are transverse cross sectional views showing other protective means formed of protective materials on the laser light transmissive probes.

For example, as shown in FIGS. 24 and 25, the back surfaces of the opposed pair of laser light transmissive probes 1, 1 are covered with metal protective materials 40, 40. Then, the base end portion of each protective material 40 is engaged to each connector 10. In this case, the engaged face of the material 40 can be fixed to the connector 10 with adhesive and the like.

On the inner surface of each protective material 40, a laser light reflecting layer (not shown) such as a plating layer of gold can be formed. Therefore, the laser light impinged onto the laser light transmissive probe 1 can reach the laser light emitting portion of the probe 1, while the laser light continues to reflect at the reflecting layer. The reflecting layer can be formed on the inner surface of the protective material 40 more easily, as compared to formation of the laser light reflecting layer on the surface of the laser light transmissive probe 1 directly.

The protective material is fabricated from steel, rustless steel, light alloy containing aluminum and the like, other metal materials, resin of tetrafluoroethylene and the like. Then, the protective material is shaped to fit on the surface of the laser light transmissive probe. Alternately, ceramics having a high strength can be coated on the back surface of the probe.

Figure 26:
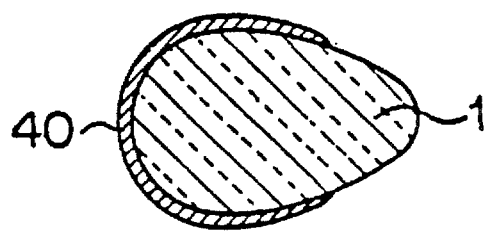
Figure 27:
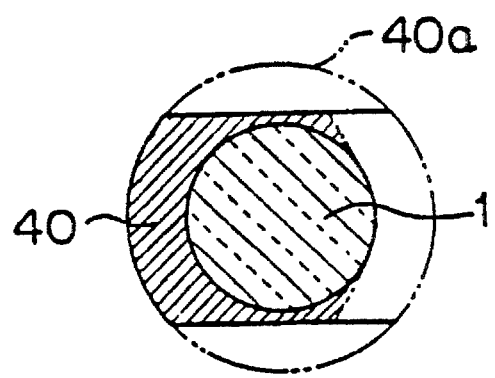

The shape of the protective material can be determined corresponding to the shape of the laser light transmissive probe. For example, as shown in FIG. 26, a protective material 40 can be formed so as to fit on the surface of the laser light transmissive probe 1 having an egg-shaped cross section. Alternately, as shown in FIG. 27, an original protective cylinder 40a shown by dashed line is provided so as to be coaxial with the laser light transmissive probe is 1. Then, the both upper and lower portions of the cylinder 40a of this figure and the emitting portion-side portion are cut off to form a protective material 40 in order to protect the probe 1.

Figure 28:
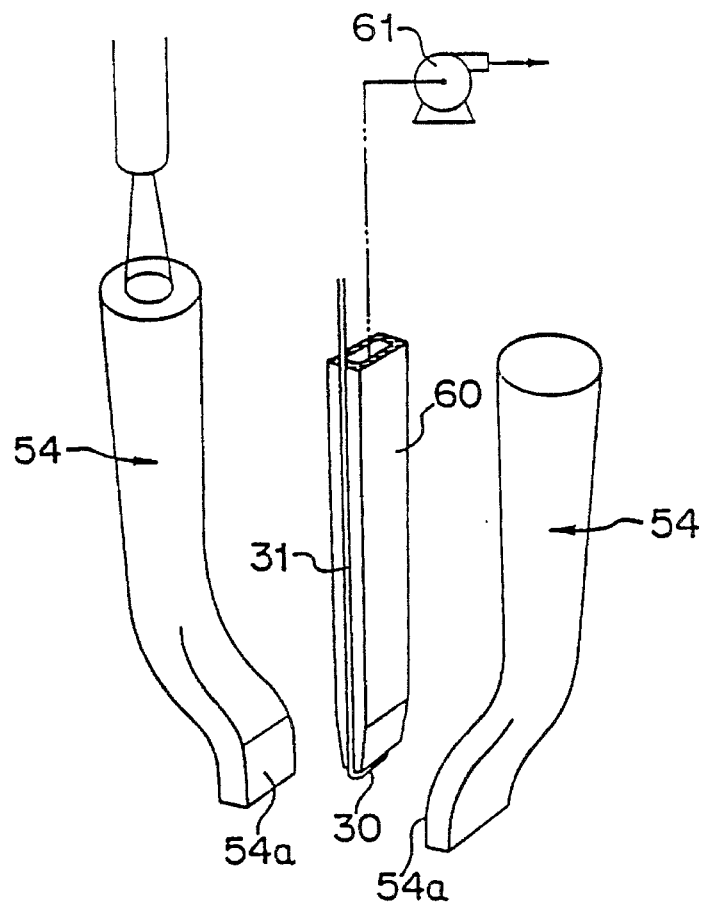
FIGS. 28 and 29 are a perspective view and a longitudinal cross sectional view of means for aspirating tissues, as provided on an opposed pair of laser light transmissive probes.
Figure 29:
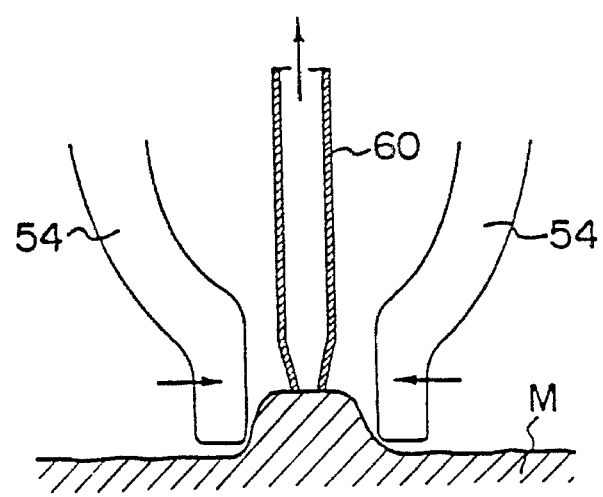

For the anastomosis of the incision lines of the tissues M or the laser light irradiation against only the projected tumor, as shown in FIGS. 28 and 29, means 60 for aspirating the target area of the tissues is preferably provided between the opposed pair of laser light transmissive probes 54, 54. In order to pinch the target area surely, at least the laser light emitting portions 54a, 54a of the opposed pair of probes 54, 54 are preferably flat. In this embodiment, means 60 for aspirating is formed by a cylinder having an opening at its upper end. Then, means 60 is connected to a suction pump 61. By activating the suction pump 61, the target area can be pulled up. In this condition, the laser light is irradiated from the flat emitting portions 54a, 54a of the opposed pair of probes 54, 54 against the target area. In order to ensure the anastomosis of the tissues, the temperature of the tissues is preferably adjusted so as to be about 60° C.–80° C. Therefore, the sensor 30 for detecting temperature and the lead wire 31 are preferably provided along the means 60 for aspirating.

Figure 30:
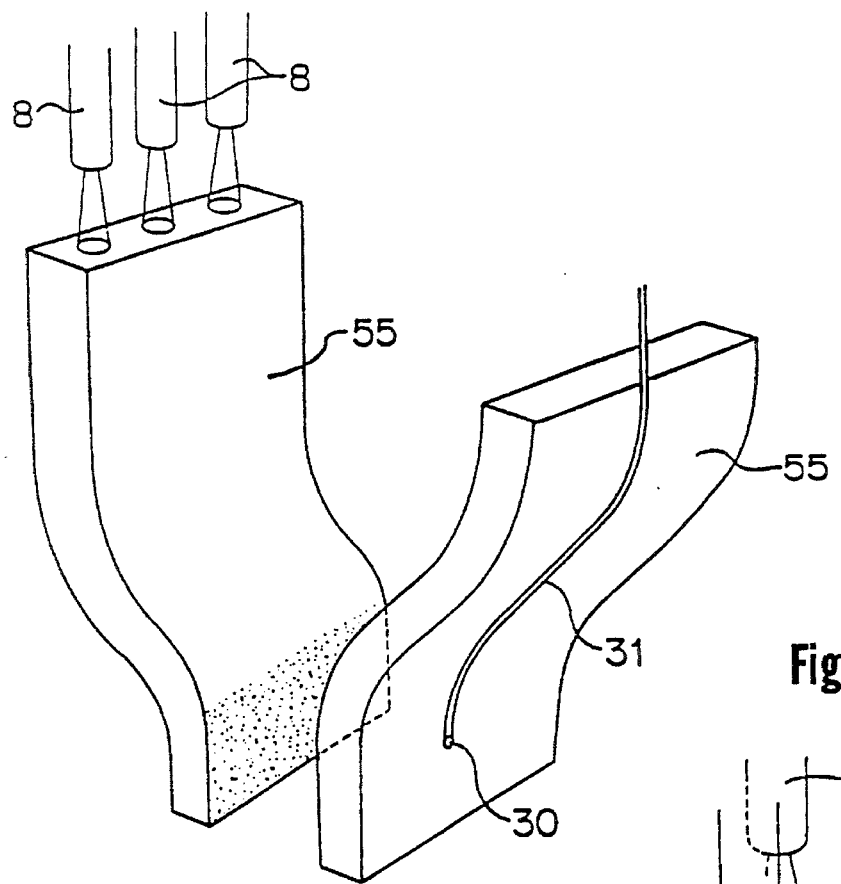
FIGS. 30 to 32 are perspective views of laser light transmissive probes having plane emitting surfaces.

For the anastomosis, as explained before, the laser light emitting portion is preferably flat. Therefore, as shown in FIG. 30, in order to form the flat emitting portions easily, the opposed pair of laser light transmissive probes 55, 55 can be formed as curved plates. However, in this embodiment, as long as single optical fiber 8 is used, the laser light can not be irradiated uniformly with respect to the vertical direction to the longitudinal direction of the laser light transmissive probe 55. Accordingly, as shown in FIG. 30, a plural number of (in this embodiment, three) optical fibers 8, 8 are preferably provided. Additionally, the scattering layer, which is indicated by marking dots in this figure, can be formed on each emitting portion.

Figure 31:
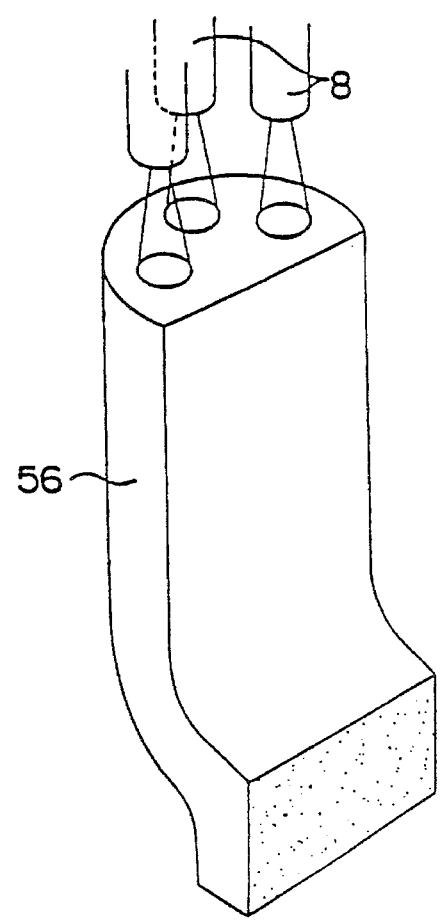

Alternately, as shown in FIG. 31, in order to form a flat laser light emitting portion easily, the laser light transmissive probe 56 can be formed so that its inner surface is curved plate-shaped. On the other hand, its back surface other than the fore end portion being opposite to the emitting portion is a portion of the side face of a cylinder. Also in this case, plural number of optical fibers 8, 8 can be provided.

Figure 32:
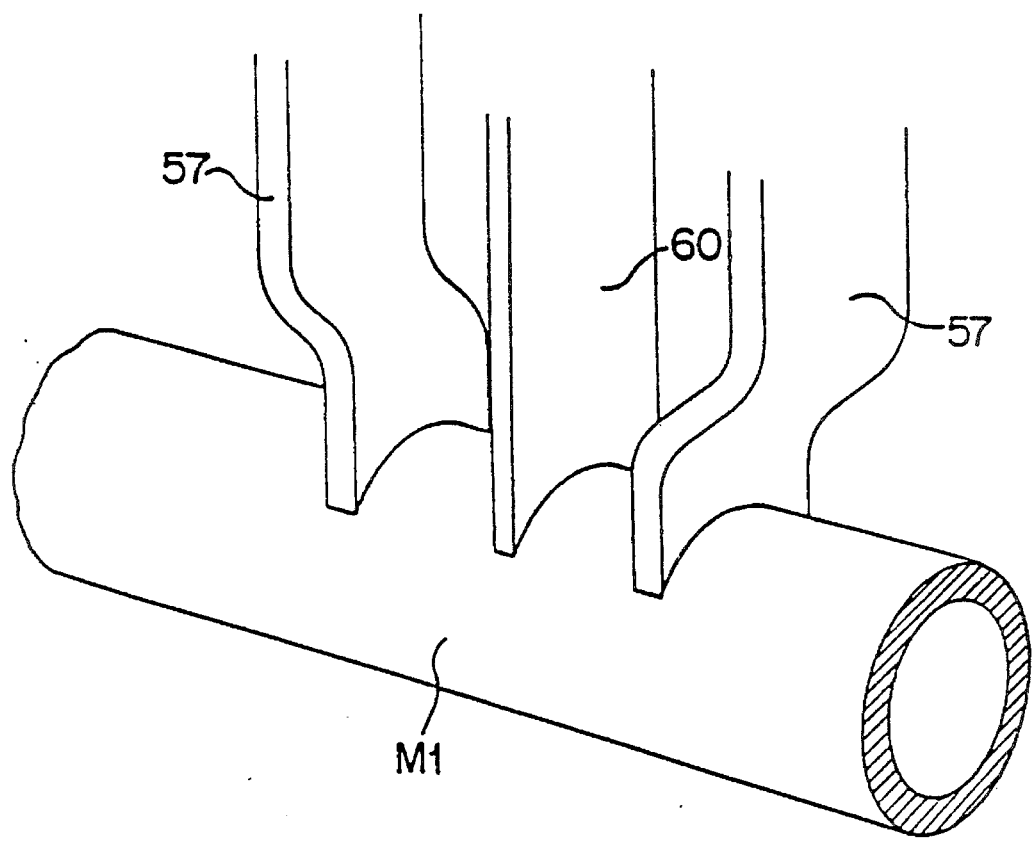

As shown in FIG. 32, when the anastomosis is carried out for tubular tissues M1, the lower end portions of an opposed pair of laser light transmissive probes 57, 57 are cut out so as to be arc-shaped. Then, means 60 for aspirating the tissues M1 is provided between the opposed pair of transmissive probes 57,57. Accordingly, the laser light is irradiated against the tubular tissues M1, while the tissues M1 are pulled up by the means 60 for aspirating.

Figure 33:
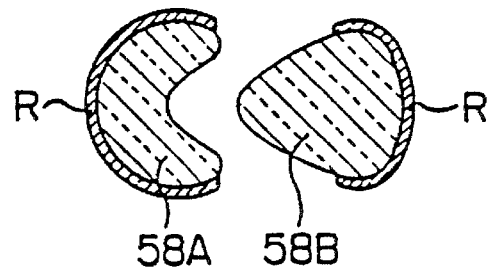
FIG. 33 is a transverse cross sectional view of an opposed pair of laser light transmissive probes wherein the shapes of the opposing surfaces are different from each other.

FIG. 33 shows an opposed pair of laser light transmissive probes 58A, 58B having different shapes respectively. Further, an opposed pair of laser light transmissive probes (not shown) can be formed so as to cross each other like a pair of scissors.

Figure 34:
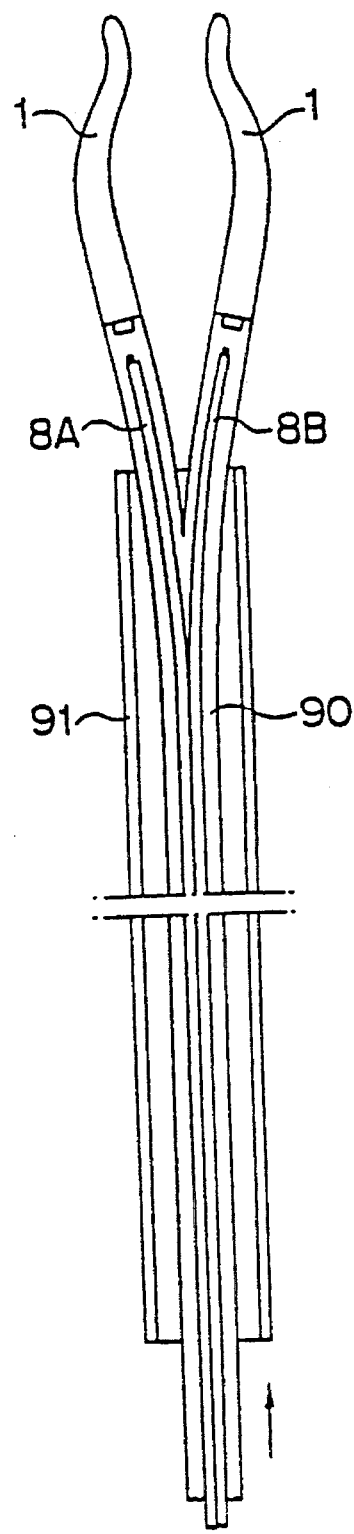
FIGS. 34 and 35 are schematic illustrations of an opposed pair of laser light transmissive probes used in an internal medical treatment.
Figure 35:
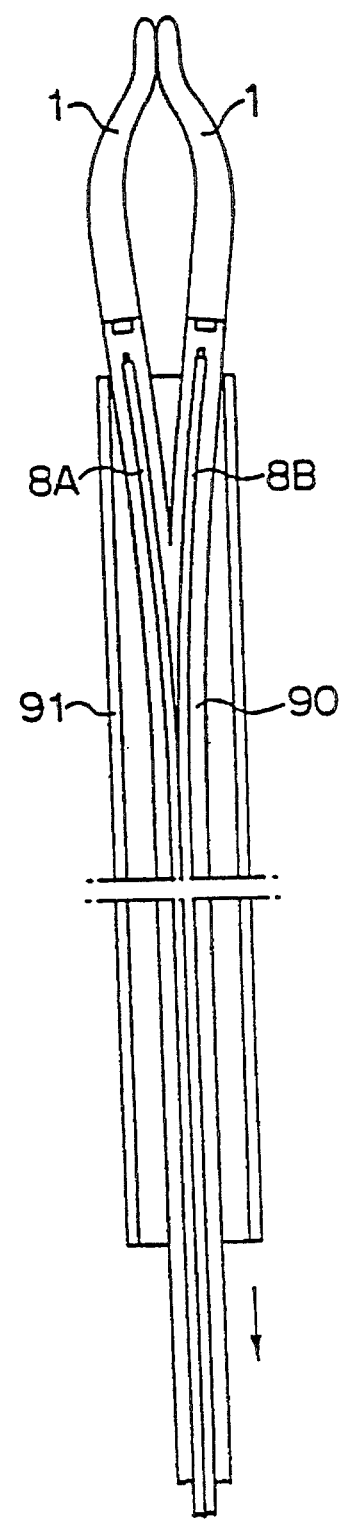

In the above mentioned embodiments, apparatus of the present invention are used in a surgical field. However, such apparatus also can be used in an internal medical field. In the internal medical field, a preferable example is as follows; As shown in FIG. 34 and 35, a holder 90 is Y-shaped. The opposed pair of laser light transmissive probes 1, 1 are fixed to the both tip ends of the branch (V-shaped) portion of the holder respectively through the connectors shown in FIG. 2. Further, the branch portion has flexibility. The holder 90 is inserted in a sheath tube 91 so that its tip ends and its base portion projects from the sheath tube 91 to be exposed. Thus, the holder 90 can be moved along the sheath tubes 91 corresponding to the pushing and pulling operations for the base portion of the holder. Therefore, as shown in FIG. 34, when the holder 90 is pushed, its branch portion is spread so that both divided portions consisting of the branch portion move apart from each other. On the other hand, as shown in FIG. 35, when the holder 90 is pulled, its branch is closed. Generally, first, an endoscope is inserted into a hole of a body. Next, this apparatus is inserted along the hole. Then, by pushing the holder 90, the opposed pair of probes 1, 1, which are put in the both divided portions respectively, are spread so as to be apart from each other. Further, when the laser light is irradiated against the target area, the holder 90 is pulled so that the opposed pair of transmissive probes 1, 1 draw close to each other. Thus, the target area of the tissues can be brought into contact with the opposed pair of transmissive probes 1, 1 from both sides. These operations are performed while the movement of apparatus in the body is observed via the endoscope. Alternately, by forming a through-hole other than the hole for observation, instead of the sheath tube 91, the holder 90 can be inserted through the through-hole.

INDUSTRIAL UTILIZATION

It will be appreciated from the foregoing description that, according to the present invention, laser light irradiation apparatus is for medical treatment, can amputate and incise the target area of the tissues with a single operation and a high level of hemostasis. At the same time, using an apparatus of the present invention, laser light is not irradiated against other normal tissues. Further, this apparatus can amputate the blood vessel without tying of the blood vessel at both sides of the target area. Accordingly, due to use of this laser light irradiation apparatus, medical operations can be finished in a short time. As a result, this apparatus can be utilized widely in the medical operations and treatments of the surgical field and the internal medical field.

What is claimed is:

1. A laser light irradiation system for use in a medical treatment, said system comprising:

a laser light generator;

transmission means for transmitting laser light from the generator;

a first probe having an axis, said first probe being formed of a laser light transmissive material for receiving laser light along the axis of the first probe from said transmission means and for emitting laser light from a light emitting surface of the first probe;

a second probe having an axis offset from the axis of said first probe, said second probe being formed of a laser light transmissive material for receiving laser light along the axis of the second probe from said transmission means and for emitting laser light from a light emitting surface of the second probe, the emitting surface of the first probe emitting at least some laser light toward the second probe, and the emitting surface of the second probe emitting at least some laser light toward the first probe;

a Y-shaped holder, wherein each laser light transmissive probe is fixed to one tip end of a flexible branch portion of the Y-shaped holder; and a tubular sheath, wherein;

said Y-shaped holder is inserted into said tubular sheath so that each tip end of a flexible branch portion projects out from a distal end of the tubular sheath and a base portion of the Y-shaped holder projects from a proximal end of said tubular sheath, and said holder can be moved back and forth along said tubular sheath to move the branch portions of the Y-shaped holder toward and away from each other, respectively, and thereby move the first probe and the second probe into and out of physical contact with each other during said medical treatment.

2. A laser light irradiation system according to claim 1, wherein:

light emerges from the light emitting surface of the first probe in a direction angularly displaced from the axis of the first probe, and light emerges from the light emitting surface of the second probe in a direction angularly displaced from the axis of the second probe.

3. A laser light irradiation system according to claim 1, wherein the light emitting surface of the first probe is projected non-axially toward the light emitting surface of the second probe.

4. A laser light irradiation system according to claim 1, wherein the light emitting surfaces of the first probe and the second probe are formed along a side face of the first probe and the second probe, respectively.

5. A laser light irradiation system according to claim 1, wherein each probe is curved.

6. A laser light irradiation system according to claim 5, wherein the curvature of each probe is such that distal ends of the probes project toward each other.

7. A laser light irradiation system according to claim 5, wherein the curvature of each probe is such that distal ends of the probes extend backward away from each other.

8. A laser light irradiation system for use in a medical treatment, said system comprising:

a laser light generator;

transmission means for transmitting laser light from the generator;

a first probe having an axis, said first probe being formed of a laser light transmissive material for receiving laser light along the axis of the first probe from said transmission means and for emitting laser light from a light emitting surface of the first probe;

a second probe having an axis offset from the axis of said first probe, said second probe being formed of a laser light transmissive material for receiving laser light along the axis of the second probe from said transmission means and for emitting laser light from a light emitting surface of the second probe, the emitting surface of the first probe emitting at least some laser light toward the second probe, and the emitting surface of the second probe emitting at least some laser light toward the first probe;

a Y-shaped holder, wherein each laser light transmissive probe is fixed to one tip end of a flexible branch portion of the Y-shaped holder, a fore end portion of said Y-shaped holder is inserted into a hole of a body through which an endoscope has been inserted, and a base portion of said holder projects from said hole such that said holder can be moved along said hole in response to an operator pushing and pulling said base portion of said holder so that when said holder is pushed, said branch portion is spread and when said holder is pulled, said branch portion is closed, to thereby move the first probe and the second probe out of and into physical contact with each other, respectively, during said medical treatment.

9. A laser light irradiation system according to claim 8, wherein:

light emerges from the light emitting surface of the first probe in a direction angularly displaced from the axis of the first probe, and light emerges from the light emitting surface of the second probe in a direction angularly displaced from the axis of the second probe.

10. A laser light irradiation system according to claim 8, wherein the light emitting surface of the first probe is projected non-axially toward the light emitting surface of the second probe.

11. A laser light irradiation system according to claim 8, wherein the light emitting surfaces of the first probe and the second probe are formed along a side face of the first probe and the second probe, respectively.

12. A laser light irradiation system according to claim 8, wherein each probe is curved.

13. A laser light irradiation system according to claim 12, wherein the curvature of each probe is such that distal ends of the probes project toward each other.

14. A laser light irradiation system according to claim 12, wherein the curvature of each probe is such that distal ends of the probes extend backward away from each other.

* * * * *